(12) United States Patent
Hawkins

(10) Patent No.: US 8,206,458 B1
(45) Date of Patent: Jun. 26, 2012

(54) PROSTHETIC SYSTEM

(76) Inventor: Ryan Hawkins, Arcadia, OK (US)

( * ) Notice: Subject to any disclaimer, the term of this patent is extended or adjusted under 35 U.S.C. 154(b) by 232 days.

(21) Appl. No.: 12/695,233

(22) Filed: Jan. 28, 2010

(51) Int. Cl.
  *A61F 2/74* (2006.01)
  *A61F 2/64* (2006.01)
  *A61F 2/66* (2006.01)
(52) U.S. Cl. .............................. 623/26; 623/39; 623/47
(58) Field of Classification Search ............ 623/26
  See application file for complete search history.

(56) References Cited

U.S. PATENT DOCUMENTS

| | | | | |
|---|---|---|---|---|
| 2,175,136 A | * | 10/1939 | Stewart | 623/26 |
| 2,519,226 A | * | 8/1950 | Coe, Jr. | 623/44 |
| 5,704,945 A | * | 1/1998 | Wagner et al. | 623/44 |
| 5,957,981 A | * | 9/1999 | Gramnas | 623/47 |
| 7,029,500 B2 | | 4/2006 | Martin | |
| 7,393,364 B2 | | 7/2008 | Martin | |
| 2004/0186591 A1 | * | 9/2004 | Lang | 623/39 |
| 2005/0203639 A1 | * | 9/2005 | Wild | 623/44 |
| 2006/0235544 A1 | * | 10/2006 | Iversen et al. | 623/26 |
| 2009/0030530 A1 | | 1/2009 | Martin | |

* cited by examiner

*Primary Examiner* — Bruce E Snow
*Assistant Examiner* — Melissa Hoban
(74) *Attorney, Agent, or Firm* — Tomlinson Rust McKinstry Grable

(57) ABSTRACT

A prosthetic device having a housing, an axle, at least three housing vanes, a flow medium and a valve. The axle is disposed within the housing and moveable independently of the housing. The axle has an axle reservoir and at least three axle vanes extending from the axle to contact the chamber wall. The three housing vanes extend from a chamber wall and contact the axle. A first opening and a second opening are formed in each axle vane. The flow medium is contained entirely within the chamber and the axle reservoir. The valve is disposed in the axle and operable in response to movement of the axle in a first direction relative to the housing to allow the flow medium to enter the axle reservoir from the chamber for storage under pressure.

13 Claims, 4 Drawing Sheets

PROSTHETIC SYSTEM

FIELD OF THE INVENTION

The present invention refers to a prosthesis system used in a prosthetic limb and more specifically to a hydraulically drive prosthetic joint.

SUMMARY OF THE INVENTION

The present invention is directed to a prosthetic device having an articulating joint. The device comprises a housing, a chamber, an axle, a flow medium and a valve. The chamber has a chamber wall disposed in the housing. The axle is disposed within the housing and configured to act as the articulating joint. The axle is moveable independently of the housing. A plurality of housing vanes extend from the chamber wall and contact the axle. A plurality of axle vanes extend from the axle to contact the chamber wall. A first opening is formed in each axle vane. The plurality of axle vanes and the plurality of housing vanes define a plurality of housing reservoirs. An axle reservoir is disposed in the axle. The flow medium is contained entirely within the chamber and the axle reservoir to communicate between the housing reservoirs and the axle reservoir through each first opening. The valve is disposed in the axle and moveable control movement of the flow medium between the housing reservoirs and the axle reservoir in response to movement of the axle relative to the housing and to regulate movement of the housing relative to the axle.

The present invention is also directed to a prosthetic device comprising a housing, an axle, at least three housing vanes, a flow medium and a valve. The housing has a chamber defined by a chamber wall. The axle is disposed within the housing and moveable independently of the housing. The axle has an axle reservoir and at least three axle vanes extending from the axle to contact the chamber wall. The three housing vanes extend from the chamber wall and contact the axle. A first opening and a second opening are formed in each axle vane. The flow medium is contained entirely within the chamber and the axle reservoir. The valve is disposed in the axle and operable in response to movement of the axle in a first direction relative to the housing to allow the flow medium to enter the axle reservoir from the chamber for storage under pressure.

Further still, the present invention is directed to a method for moving a prosthetic device. The method comprises providing a prosthetic joint having a housing and an axle disposed within the housing and moveable independently of the housing. Either the housing or axle is connected to a stump and the other connected to a prosthesis. An external force is placed on the prosthesis to move the housing from a first position to a second position relative to the axle. A flow medium is moved from a first housing chamber and a second housing chamber to a third housing chamber for storage under pressure in response to movement of the housing in a first direction. The external force is removed from the prosthesis to release the flow medium from the third housing and automatically move the housing from the second position to the first position.

DESCRIPTION OF THE INVENTION

Prosthetic devices provide a valuable service for amputees and provide an enhanced quality of life amputees would otherwise not enjoy. Currently, research in prosthetic devices is focused on providing natural movement and control of a prosthetic device. Devices and systems have been developed to enhance movement of prosthetic joints. However, there remains a need to improved devices that enable controlled movement of prosthetics limbs.

Figure 1:
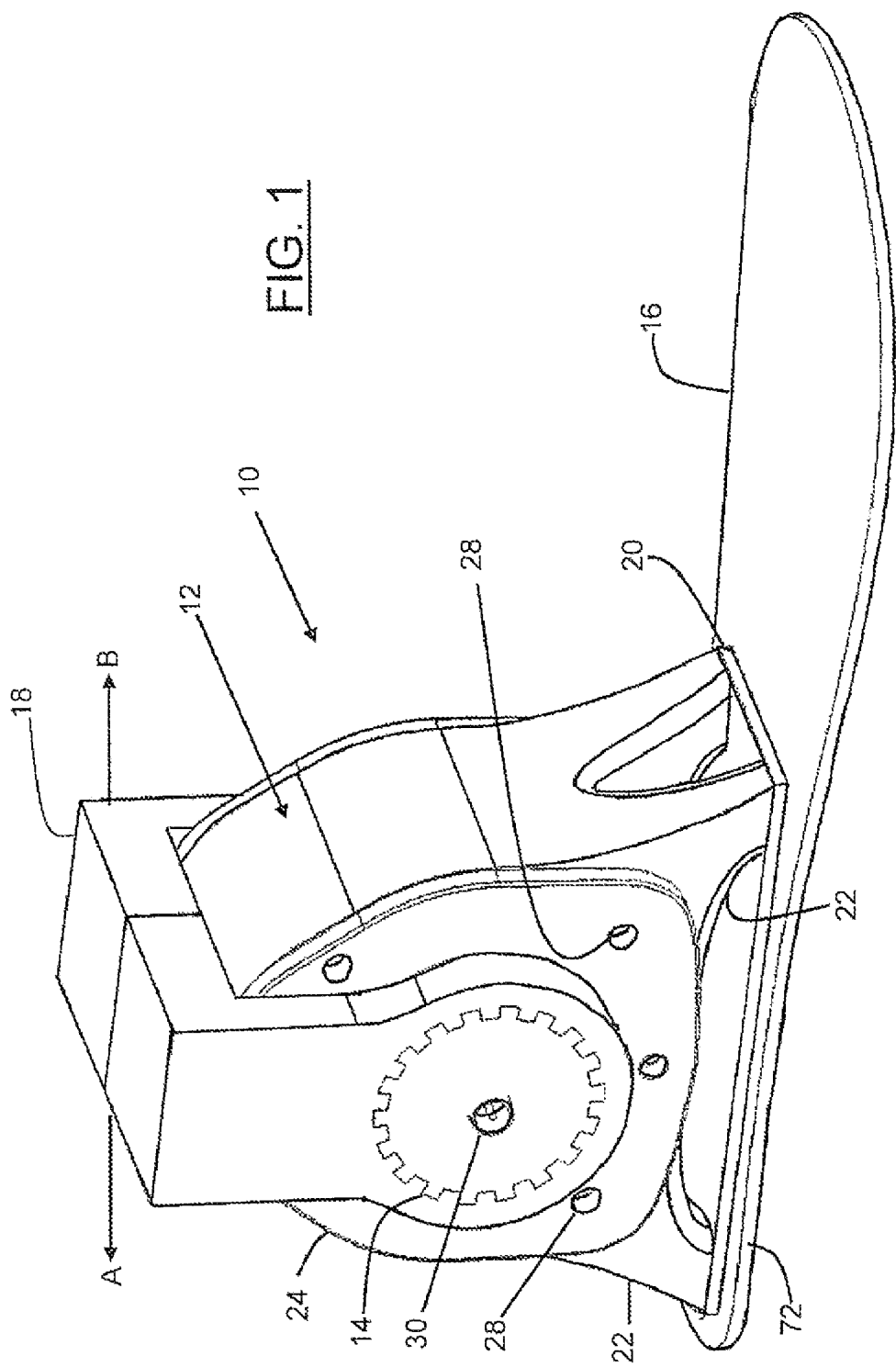
FIG. 1 is a perspective view of a prosthetic device joint in accordance with the present invention. The joint of FIG. 1 is shown used as an ankle joint in a prosthetic foot.

Turning now to the Figures and specifically to FIG. 1, there is shown therein a prosthetic device 10 of the present invention. The prosthetic device 10 comprises a housing 12, an axle 14, a prosthetic foot 16, and a limb connector 18 attached to the axle. A platform 20 is connected to a plurality of housing feet 22 which is then connected to the prosthetic foot 16. The platform 20 provides structural support for the housing 12. One skilled in the art will appreciate that the exterior of the housing 12 may be configured differently for different and varied applications without departing from the sprit of the present invention. A cover 24 is connected to a housing body 26 using a fastener (not shown) secured in holes 28.

The axle 14 is splined to engage a matingly splined portion of the limb connector. The axle 14 is shown with an as yet to be described valve stein 30. The splined connected between the limb connector 18 and axle 14 allows for movement of the limb connector and axle together. Movement of the limb connector 18 and axle 14 is independent of the housing 12 and prosthetic foot 16.

Figure 2:
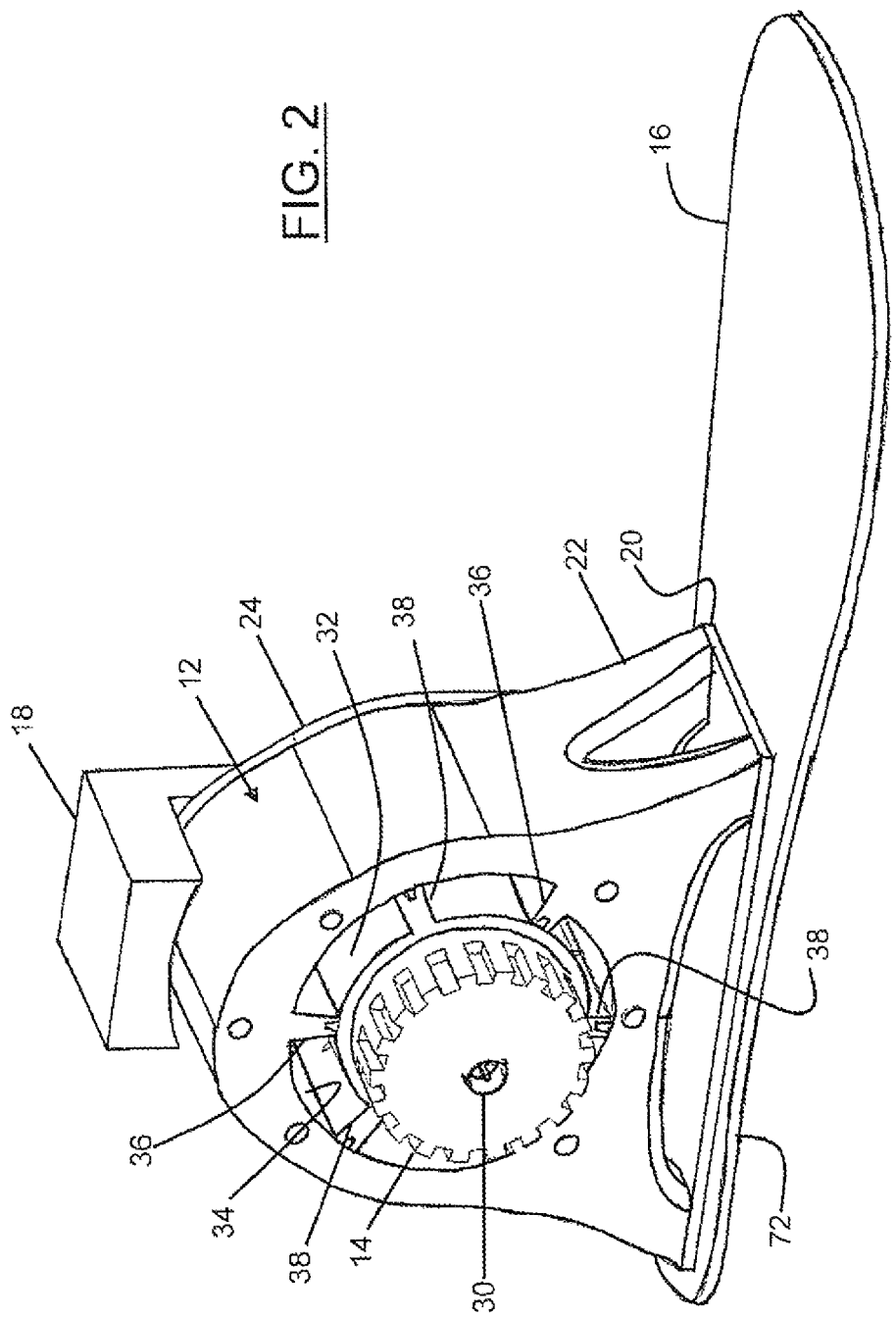
FIG. 2 is a partial cut-away view of the prosthetic joint of FIG. 1 showing the housing chamber, axle vanes and housing vanes.

Turning now to FIG. 2, there is shown therein the prosthetic device 10 of FIG. 1 in a partially cut-away view. The device 10 of FIG. 2 shows the prosthetic foot 16 connected to the platform 20. As discussed above, the platform 20 is connected to the housing feet 22 for movement therewith. The housing 12 is shown with the housing cover 24 removed from one side of the housing to show a chamber 32 having a chamber wall 34. A plurality of housing vanes 36 extend from the chamber wall 34 to contact the axle 14. The housing vanes 36 define a plurality of housing reservoirs within the chamber 32.

The axle 14 is disposed within the housing and extends beyond either side of the housing 12 and housing covers 24. The axle 14 is configured to act as an articulating joint for the prosthetic device and is moveable independently of the housing 12. The portion of the axle 14 extending outside the housing 12 may comprise splines formed to matingly engage similarly form splines of the limb connector 18. A plurality of axle vanes 38 extend from the axle 14 to contact the chamber wall 34. A select axle vane 38 is moveable within its housing reservoir in response to movement of a flow medium (not shown) or of the limb connector 18 and axle 14 relative to the housing 12.

Figure 3:
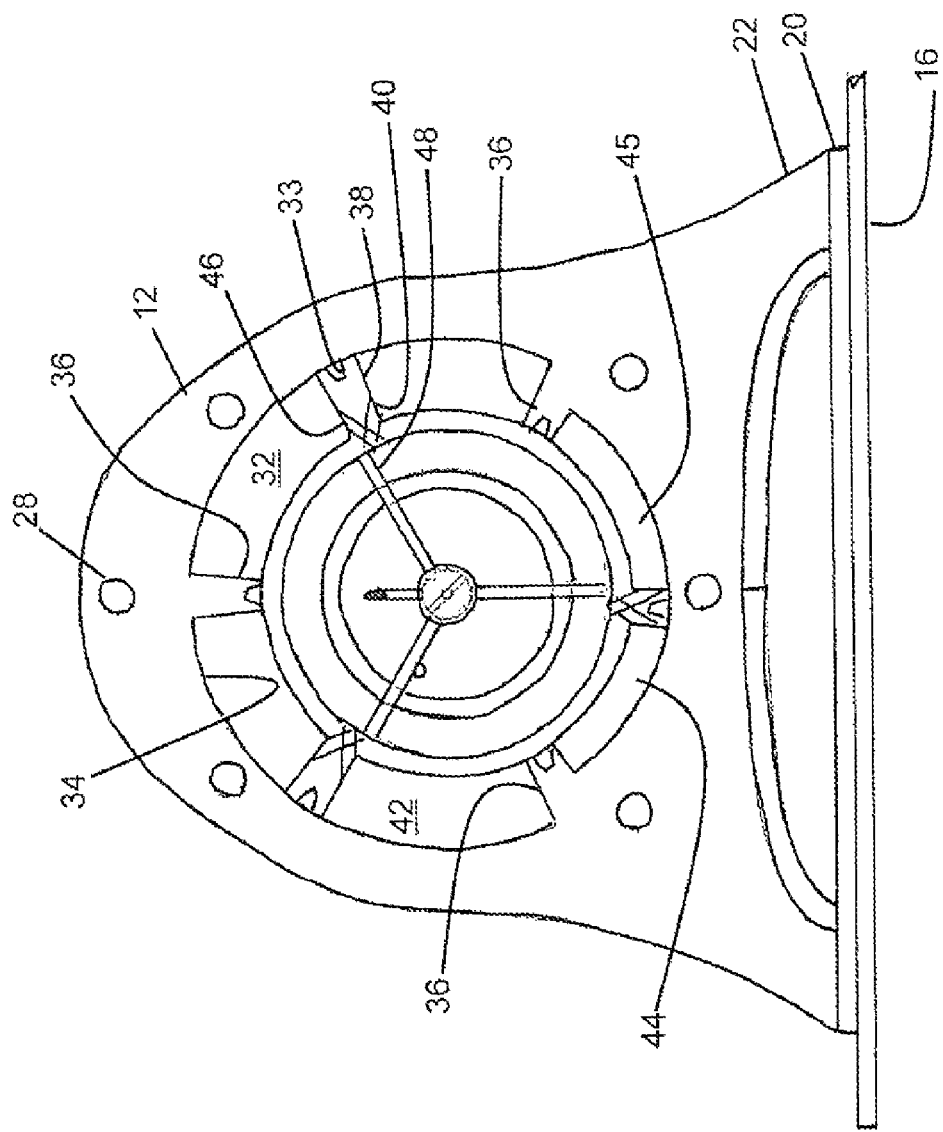
FIG. 3 is a side view of the prosthetic joint of the present invention showing a plurality of channels connecting the chamber to an axle reservoir.

Turning to FIG. 3, each axle vane 38 has a first opening 40 formed in the axle vane. Each axle vane 38 comprises a notch 33 formed to hold a vane seal (not shown) to hermetically seal housing reservoirs 32, 42, and 44. A second opening 46 is formed in each axle vane 38 is positioned opposite the first opening 40. Upon movement of the axle 14 in direction A the flow medium is forced into openings 40 from reservoirs 32 and 42 and into passage way 48. The flow medium travels through passage 48 and into reservoir 44 where it is stored for later use. Excess flow medium may be stored in an axle reservoir, to be discussed later herein. A sensor (not shown) in reservoir 44 controls a valve (FIG. 4) and directs the flow medium into either the reservoir 44 or the axle reservoir (FIG. 4) depending on the pressure reading. The movement of the axle vanes 38 in direction A creates a vacuum in reservoirs 32, 42 and 45. The vacuum and pressurized fluid in reservoir 44 causes the axle to move in direction B to reset the axle relative to the housing when the foot is lifted from the ground. Alternatively, the flow medium may move through the first opening and out of the second opening 46 into reservoirs 32 and 42.

Reservoirs 44 and 45 are generally smaller than reservoirs 32 and 42. During the heel strike portion of an individuals gait the flow medium moves from reservoirs 32 and 42 into the central reservoir. The central valve regulates the flow of the medium from the housing reservoirs 42 and 32 to the central reservoir to make efficient use of the volumetric efficiency of the larger reservoirs 42 and 32 versus the smaller reservoirs 44 and 45 when the individual lifts the foot and needs to reposition it. The flow medium is routed from the central reservoir to the smaller reservoir 44 and 45. This arrangement allows the prosthetic device to gain stored energy during each step. The stored energy is used for phases of the individual's gait where energy is needed to move the axle relative to the housing.

Figure 4:
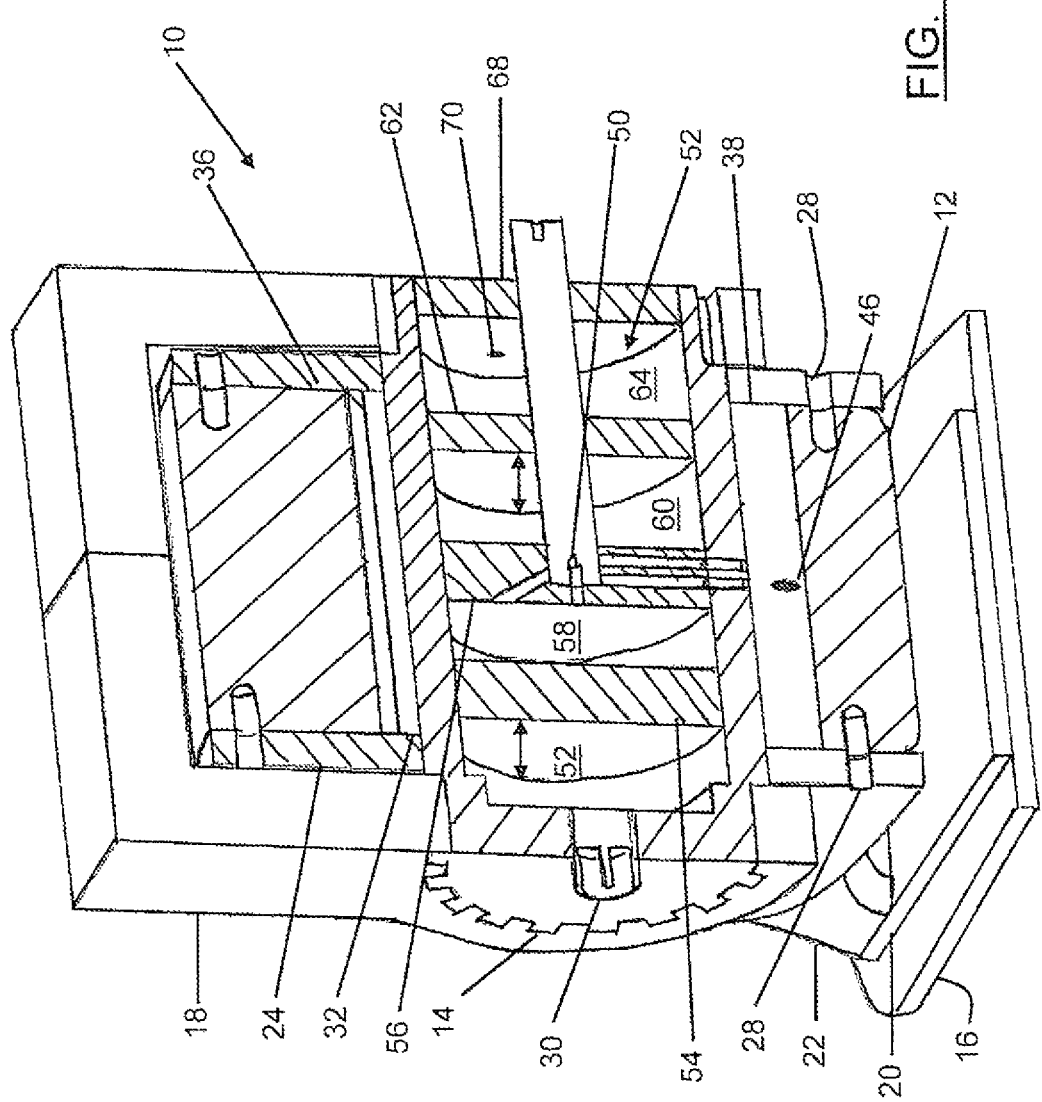
FIG. 4 is a perspective view of a cross-section of the joint of the present invention.

With reference now to FIG. 4, a sectional view of the prosthetic device 10 is shown. FIG. 4 shows the axle 14 in more detail. As discussed, the housing 12 is connected to the prosthetic foot 16 by platform 20 on feet 22. The housing 12 supports the axle 14 within the chamber 32. The axle 14 may comprise a valve 50 centrally located within an axle reservoir 52. The valve 50 may comprises a rotating spool valve moveable between an open position and a closed position to control movement of the flow medium between the housing reservoirs and the axle reservoir 52 in response to movement of the axle relative to the housing. The axle reservoir 52 may be divided into multiple chambers, each chamber having a different function.

Chamber 52 is defined by the axle and a moveable partition 54. Chamber 52 may contain a non-corrosive gas such as nitrogen at pressure. The gas may be fed into chamber 52 through valve stem 30. Partition 54 and central body 56 define chamber 58 which contains pressurized flow medium. Flow medium is injected and removed from chamber 58 through a pair of openings in response to operation of valve 50. Excess flow medium is stored in chamber 60 at low or atmospheric pressure. Chamber 60 is defined by central body 56 and movable partition 62. Movable partition 62 and an end cap 68 define an air reservoir 64 holding ambient air. Air may enter the air reservoir 64 through an air hole 70 in response to movement of partition 62. Thus, the flow medium as described herein, may comprise a hydraulic fluid contained entirely within the housing chamber 32 and the axle reservoir to communicate between the housing reservoirs and the axle reservoir through the series of passages formed in the axle and axle vanes.

One skilled in the art will appreciate that a pylon (not shown) may be connected to the limb connector 18. The pylon may comprise a storage device adapted to contain compressed nitrogen gas. The compressed gas may be metered into a high pressure reservoir to provide powered movement of the axle relative to the housing. The gas compresses the flow medium with each step to provide powered movement of the device. Alternatively, an external air pump may be used to pump air into the air reservoir. This air pump may be powered by a portable power source contained within the prosthetic device.

In operation, an external force is placed on the heel 72 (FIG. 1) of the prosthetic foot 16 to rotate the axle 14 and limb connector 18 in direction A relative to the housing 12. As the individual using the prosthetic device continues their step, the limb connector and axle are moved in direction B (FIG. 1). Movement of the axle 14 in direction B causes the axle vanes 38 to move and pushes the flow medium into openings 40 and into reservoir 44 through passages 48 (FIG. 3). When the individual lifts the prosthetic device 10 from the ground surface, the external force is removes from the prosthesis and the flow medium is released from the reservoir 44 to automatically move the housing from compressed position back to a neutral position for the individuals next step.

Various modifications in the design and operation of the present invention are contemplated without departing from the spirit of the invention. Thus, while the principal preferred construction and modes of operation of the invention have been illustrated and described in what is now considered to represent its best embodiments it should be understood that the invention may be practiced otherwise than as specifically illustrated and described.

The invention claimed is:

1. A prosthetic device having an articulating joint, the device comprising:
   a housing;
   a chamber having a chamber wall disposed in the housing;
   an axle disposed within the housing configured to act as the articulating joint and moveable independently of the housing;
   a plurality of housing vanes extending from the chamber wall to contact the axle;
   a plurality of axle vanes extending from the axle to contact the chamber wall;
   a first opening formed in each axle vane;
   wherein the plurality of axle vanes and the plurality of housing vanes define a plurality of housing reservoirs;
   an axle reservoir disposed in the axle;
   a flow medium contained entirely within the chamber and the axle reservoir to communicate between the housing reservoirs and the axle reservoir through each first opening; and
   a valve disposed in the axle and moveable to regulate movement of the flow medium between the housing reservoirs and the axle reservoir in response to movement of the axle relative to the housing.

2. The prosthetic device of claim 1 further comprising a means for attaching the housing to a prosthetic foot.

3. The prosthetic device of claim 1 further comprising a limb connector attached to the axle and moveable with the axle and independently of the housing.

4. The prosthetic device of claim 1 further comprising a hermetic seal between the housing vane and the axle.

5. The prosthetic device of claim 4 further comprising a hermetic seal between the axle vane and the chamber wall.

6. The prosthetic device of claim 1 further comprising a second opening formed in the axle vane and opposing the first opening, wherein the flow medium moves through the second opening in response to movement of the axle relative to the housing.

7. The prosthetic device of claim 1 wherein the plurality axle vanes extend along an entire length of the axle and are spaced equidistant about a circumference of the axle.

8. A prosthetic device comprising:
   a housing having a chamber defined by a chamber wall;

an axle disposed within the housing and moveable independently of the housing, the axle having an axle reservoir and at least three axle vanes extending from the axle to contact the chamber wall;

at least three housing vanes extending from the chamber wall to contact the axle;

a first opening and a second opening formed in each axle vane;

a flow medium contained entirely within the chamber and the axle reservoir; and a valve disposed in the axle and moveable to regulate movement of the flow medium when the axle moves in a first direction relative to the housing to allow the flow medium to enter the axle reservoir from the chamber for storage under pressure.

9. The prosthetic device of claim 8 further comprising a means for attaching the housing to a prosthetic foot.

10. The prosthetic device of claim 8 further comprising a limb connector attached to the axle and moveable with the axle and independently of the housing.

11. The prosthetic device of claim 8 wherein the axle vane and axle are integrally formed.

12. The prosthetic device of claim 8 wherein the axle reservoir comprises:

a gas chamber;

a pressurized flow medium chamber;

a non-pressurized flow medium chamber; and an air chamber.

13. The prosthetic device of claim 12 wherein the axle comprises:

a valve core in fluid communication with the pressurized flow medium chamber; and a valve stem in fluid communication with the gas chamber.

* * * * *